(12) United States Patent
Yang et al.

(10) Patent No.: US 9,156,861 B2
(45) Date of Patent: Oct. 13, 2015

(54) METHOD FOR PREPARING TRIALKOXYSILANE

(75) Inventors: Se In Yang, Seongnam-si (KR); Yong Il Kim, Incheon (KR); Kyung Yeol Kim, Seoul (KR); Deok Yun Kim, Seongnam-si (KR); Ashurov Khatam, Tashkent (UZ); Abdurakhmanov Boris, Tashkent (UZ); Rotshteyn Vladimir, Tashkent (UZ); Salikhov Shavkat, Tashkent (UZ); Ashurova Khekayat, Tashkent (UZ); Salimboev Akmal, Tashkent viloyat (UZ); Azizov Sultan, Tashkent (UZ); Saidov Sabir, Tashkent (UZ)

(73) Assignees: OCI COMPANY LTD., Seoul (KR); INSTITUTION OF ION-PLASMA AND LASER TECHNOLOGIES, Tashkent (UZ)

( * ) Notice: Subject to any disclaimer, the term of this patent is extended or adjusted under 35 U.S.C. 154(b) by 0 days.

(21) Appl. No.: 14/241,581

(22) PCT Filed: Mar. 30, 2012

(86) PCT No.: PCT/KR2012/002428
§ 371 (c)(1),
(2), (4) Date: Feb. 27, 2014

(87) PCT Pub. No.: WO2013/035956
PCT Pub. Date: Mar. 14, 2013

(65) Prior Publication Data
US 2014/0364639 A1 Dec. 11, 2014

(30) Foreign Application Priority Data
Sep. 6, 2011 (UZ) .................................... 20110393

(51) Int. Cl.
C07F 7/00 (2006.01)
C07F 7/02 (2006.01)
(Continued)

(52) U.S. Cl.
CPC ................. $C07F\ 7/025$ (2013.01); $B01J\ 23/72$ (2013.01); $C07F\ 7/04$ (2013.01)

(58) Field of Classification Search
CPC .............. C07F 7/025; C07F 7/04; B01J 23/72
USPC ......................................................... 556/472
See application file for complete search history.

(56) References Cited

U.S. PATENT DOCUMENTS

| 2,380,997 A | 8/1945 | Patnode |
| 2,473,260 A | 6/1949 | Rochow |

(Continued)

FOREIGN PATENT DOCUMENTS

| EP | 0517398 A1 | 12/1992 |
| GB | 2263113 A | 7/1993 |

(Continued)

OTHER PUBLICATIONS

International Search Report for PCT/KR2012/002428 mailed on Oct. 18, 2012.

*Primary Examiner* — Porfirio Nazario Gonzalez
(74) *Attorney, Agent, or Firm* — Lowe Hauptman & Ham, LLP

(57) ABSTRACT

The present invention relates to a method for preparing SiH($OR_3$)-type trialkoxysilane (wherein, R is a C1-C3 methyl, ethyl, propyl or isopropyl group), and more specifically, the method comprises the steps of: preventing the oxidation of a silicon surface by pulverizing raw silicon material in a solvent environment without contact with the air so that the initial induction period of the direct synthesis of trialkoxysilane is dramatically reduced; and removing impurities from a reaction environment by continuously selecting a part of the solvent through a membrane filter provided in a reactor body.

12 Claims, 1 Drawing Sheet

(51) Int. Cl.
*C07F 7/04* (2006.01)
*B01J 23/72* (2006.01)

(56) References Cited

U.S. PATENT DOCUMENTS

| | | |
|---|---|---|
| 3,072,700 A | 1/1963 | de Wit |
| 3,641,077 A | 2/1972 | Rochow |
| 3,775,457 A | 11/1973 | Muraoka et al. |
| 4,314,908 A | 2/1982 | Downing et al. |
| 4,487,949 A | 12/1984 | Mallon |
| 4,727,173 A | 2/1988 | Mendicino |
| 4,762,939 A | 8/1988 | Mendicino |
| 4,931,578 A | 6/1990 | Ohta et al. |
| 5,084,590 A | 1/1992 | Ritscher et al. |
| 5,166,384 A | 11/1992 | Bailey et al. |
| 5,177,234 A | 1/1993 | Nguyen et al. |
| 5,260,471 A | 11/1993 | Yamada et al. |
| 5,362,897 A | 11/1994 | Harada et al. |
| 5,783,720 A | 7/1998 | Mendicino et al. |
| 6,090,965 A | 7/2000 | Lewis et al. |
| 6,580,000 B1 | 6/2003 | Anderson et al. |

FOREIGN PATENT DOCUMENTS

| | | |
|---|---|---|
| JP | S5034540 B | 11/1975 |
| JP | S511692 B | 1/1976 |
| JP | 05178864 A | 7/1993 |
| JP | 06065258 A | 3/1994 |
| JP | 06312992 A | 11/1994 |
| JP | 06312994 A | 11/1994 |
| KR | 1020030077594 A | 10/2003 |
| KR | 100625148 B1 | 9/2006 |
| RU | 2235726 C1 | 9/2004 |
| WO | 2007032865 A2 | 3/2007 |

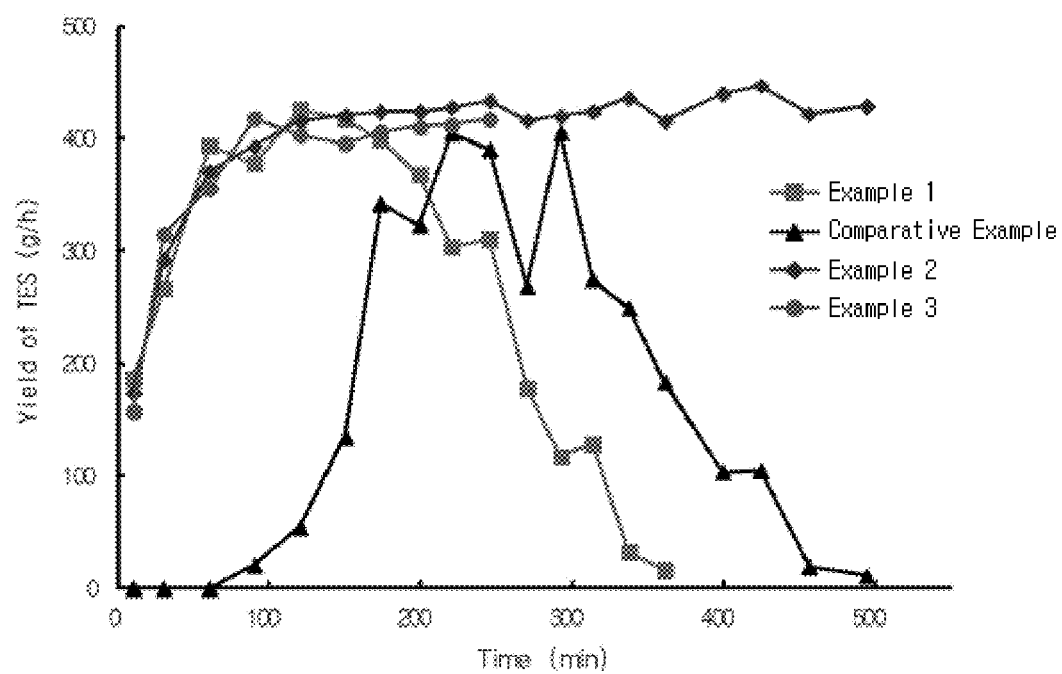

METHOD FOR PREPARING TRIALKOXYSILANE

CROSS REFERENCE TO RELATED APPLICATION

This application claims the priority of Uzbekistan Patent Application No. IAP 20110393 filed on Sep. 6, 2011 in the Korean Patent and Trademark Office. Further, this application is the National Phase application of International Application No. PCT/KR2012/002428 filed on Mar. 30, 2012, which is incorporated herein by reference in its entirety.

TECHNICAL FIELD

The present invention relates to a method for preparing trialkoxysilane, and more particularly, to a method for preparing $SiH(OR)_3$-type trialkoxysilane (wherein, R is methyl, ethyl, propyl or isopropyl group having 1 to 3 carbon atoms).

BACKGROUND ART

Herein, the number in parenthesis [ ] refers to the number of related art document cited for reference.

Trialkoxysilane is used in various fields such as production of siliceous oligomer, monosilane, silicon for solar energy or semiconductor, and the like, and for synthesis of such trialkoxysilane, two basic methods are used.

First method is to synthesize trialkoxysilane in fixed bed or fluidized bed under a vapor-gas environment. The method for preparation in a vapor-gas environment is to pass alcohol vapor through a silicon powder layer including catalyst in fixed bed or fluidized bed. However, a fixed bed reactor is not widely-used because of the difficulty of maintenance of uniformly distributed temperature throughout the whole reactor volume. In case of direct synthesis in fluidized bed, such disadvantage is avoidable.

In [1], a method for diluting gas in alcohol vapor may be used to prevent or minimize that temperature in fluidized bed reaches peak. As a diluting gas, argon, nitrogen, helium, neon, hydrogen, and the like may be used. However, if additional material is applied, production cost, and also losses of trialkoxysilane and alcohol caused by the carryover of inert gas are increased. Meanwhile, the output power of desired trialkoxysilane is improved by synthesis under a lower pressure. In this case, conversion rate of silicon is 90%, selectivity of silicon is 84.2%, while under a normal pressure, 65%, and 48.8%, respectively. However, there is a disadvantage in that as pressure is lowered, reaction rate decreases, and as a result, productivity is deteriorated.

[2] suggests passing hydrogen with alcohol vapor through contact mass. If hydrogen is applied to the technical process of preparation of trialkoxysilane, additional preparing and purifying parts for hydrogen are needed, which increases preparation cost. When contact mass was activated with nitrogen, and zinc was added as an accelerator at reaction temperature of 280° C. or less, the content of triethoxysilane in reacting materials was 87%, but the conversion rate of silicon was very low, 23%.

It is preferred to stepwise carry out the activation of contact mass including silicon and a catalyst, at 450° C. or less in [1], or at 300-350° C. in [2] and [5], under a nitrogen or other inert gas atmosphere.

[6] to [9] suggest a method of applying hydrogen for silicon and catalyst activation. Activation using hydrogen is carried out at about 400° C. in fixed bed or fluidized bed. The mixture of silicon and catalyst contains 1.5% or more of copper. However, any information as to the resulting selectivity, reactivity, and reaction stability is not presented.

In [1] to [9], as a result of synthesis in fluidized bed for obtaining triethoxysilane, in case the reaction is carried out under atmospheric pressure, the yield of triethoxysilane and the conversion rate of silicon are not high, and in case the reaction is carried out under low pressure, main synthesis index is improved, but such advantage is offset by consequent technical features. In addition, in case liquefied material is additionally injected with alcohol, some numerical values increase, but some problems arise in the synthesis process of trialkoxysilane in fluidized bed, and minor carryover of silicon and catalyst necessarily occurs, thereby requiring an additional filtering process for final product.

Second method is to carry out a direct reaction between silicon and alcohol in suspension state in the liquid solvent environment of a reactor equipped with a stirring device. This method is recently widely used, because in case of using a solvent, the temperature of reaction mixture may be uniformly maintained to greatly reduce the possibility of overheating reaction environment, and prevent side reaction, thereby raising the selectivity of trialkoxysilane and the conversion rate of silicon.

In the synthesis of trialkoxysilane, the temperature is maintained high, up to 300° C., and thus, a solvent used in the synthesis should not be decomposed at such temperature. Solvent should effectively maintain uniform temperature in reaction system. In addition, it should not generate oxidation at reaction temperature ranging 100-300° C., as well as highly disperse the powder.

[10] and [11] suggest using alkylated benzene, and [12] suggests using alkylated naphthalene-"THERMINOL" oil. Details of high temperature solvents of THERMINOL® 59, 60, 66, DOWTHERM® HT, MARLOTHERM® S, MARLOTHERM® and other trademarks are described in [13] and [25].

[13], [14] and [15] suggest that the amount of solvent used in synthesis should be 1:2-4:1 of solvent:silicon, preferably 1:1-2:1.

In [16]-[20], it takes a considerable induction period to activate the reaction after pouring reaction raw materials of silicon and alcohol, which may last for 1 hour to 12 hours. The main reason for generation of induction period is an oxide film on the surface of silicon. In order to reduce induction period, it is suggested that activation step should be added in the synthesis process of trialkoxysilane.

[13] reviews the activation process in very detail. Activation may be carried out in the corresponding reactor in which the reaction proceeds or a separate equipment. It is preferred to move silicon activated in a separate equipment from dry neutral environment to the reactor. Activation is carried out at 20 to 400° C., preferably 150 to 300° C. It is suggested that hydrogen and nitrogen are used together as activating gas, and silicon is activated by methanol for the reaction with ethanol, because methanol has higher reaction activity to silicon than ethanol or higher alcohol. For example, if 5% of methanol is added to ethanol, reaction rate significantly increases. Herein, a reaction suspension containing 1 kg of silicon, 14.1 g of copper hydroxide, and 2.1 kg of solvent Marlotherm®S was activated at 150 to 250° C. for 65 minutes using hydrogen and nitrogen. Methanol was fed at 250° C. for 5 hours at a rate of 4.3 g/min. Thereafter, the temperature was lowered to 230° C., the feed of methanol was stopped, and ethanol was fed at the same rate, wherein the feed of hydrogen was stopped, and that of nitrogen was sustained. The total amount of activating material is stoichiometrically calculated, and enough to convert divalent or monovalent copper catalyst to free copper. It takes considerable time for an actual activity process, and it is asserted that it is caused by a large silicon-copper mass surface (fine particle diameter of silicon 50-300 μm). Meanwhile, a special condition as to granularity of used catalyst is required. Fine particle size should range 1-100 μm, preferably 0.1-50 μm, more preferably 0.1-30 μm. At the same time, specific surface area of the catalyst within a raw material is 0.1-2 $m^2/g$, preferably 10-50 $m^2/g$. Direct synthesis reaction of silicon using alcohol is feasible both in periodic mode and continuous mode. In periodic mode, all silicon is put into a reactor early in the process, while alcohol is continuously fed until all silicon is reacted. Depending on the output, it is also possible that a certain amount of silicon is fed in turn, and alcohol is continuously fed. In case of a reactor in continuous mode, only silicon or silicon containing a catalyst is added after starting process. In this case, the content of catalyst is minimum, or controlled so that side reaction decomposing alcohol does not occur. Reaction temperature is 150° C. or more, but not higher than the temperature where the decomposition of alcohol and solvent occurs. It is preferred to carry out the reaction at 200-260° C. In methanol reaction, 220-250° C. is preferred, and in ethanol reaction, 200-240° C. is preferred. It is possible to carry out the direct synthesis reaction of trialkoxysilane at both high pressure and low pressure, but atmospheric pressure is preferred.

[21] and [22] suggest treating powdered silicon with hydrogen fluoride in order to remove an oxide film on silicon surface prior to working for shortening induction period.

[10] and [22] suggest activating reaction mass by maintaining high temperature under a nitrogen, argon, and other inert environment, and [23] suggests pre-mixing silicon and a catalyst in mill for 8 hours in an inert atmospheric condition, respectively.

[21] suggests injecting alkyl chloride, hydrogen chloride, or ammonium chloride for activating silicon prior to synthesis, and [24] suggests injecting halides such as $NH_4HF_2$. However, in case materials such as halide, alkyl halide and methanol are injected to a reactor prior to synthesis, a distillation step of aimed material is added for removing impurities in aimed material, which means that the preparation technique of trialkoxysilane becomes complicated.

Therefore, it is appreciated that induction period in a direct synthesis process of trialkoxysilane is not simply understood, and effective solution therefor does not exist. In case of injecting an additional reagent in synthesis process, the reagent should be removed from the final product, which adds a further step, and consequently makes the preparation technique of trialkoxysilane complicated and its production cost high.

In [11], [13], [14], [17] and [21], the main synthesis reaction of trialkoxysilane is accompanied by a side reaction which may form oligoalkoxysiloxane, moisture and other side reaction products, and they may be gradually accumulated under reaction environment to lower reaction rate of synthesis process. In [14], the reason is that metal being in the form of impurity in the synthesis of silicon may be contained in a catalyst and used. Copper metal is accumulated in a solvent component as a result of decomposition of a catalyst. If silicon and trialkoxysilane containing such remaining silicon and impurities are accumulated, reaction rate decreases. In such case, in order to continuously use a solvent in synthesis process of trialkoxysilane, the solvent must be regenerated.

[16] suggests using aluminium (0.01-10%, preferably 0.1-2%), [2] suggests using zinc, [25] suggests using an organic or inorganic compound possessing at least one phosphorus-oxygen bond, as an accelerators of reaction forming trialkoxysilane for increasing efficiency of main synthesis index of trialkoxysilane. However, any information about the effects therefrom is not provided.

[1] suggests a process for producing trialkoxysilane comprising pulverizing silicon and performing interaction of ground silicon and alcohol under the action of a catalyst. Industrial silicon ground to a particle size of 500 μm in the air is used as a feedstock. Ethanol and methanol are used as alcohol reagents, and a copper-containing compound such as copper (I) chloride (CuCl) is used as a catalyst. They are mixed with ground silicon, and heated at 300° C. or less for several hours, thereby activating the catalyst to activate technical interaction of alcohol and silicon. Such technical method is also used in other methods similar to that of [1]. Together with this, for the purpose of interaction of silicon and alcohol, an additional catalyst in the form of halides is applied, and as organic and inorganic materials containing a halogen component, chlorides, fluorides, methyl bromide, ethyl bromide, ethylene trichloride, hydrogen fluoride (HF), hydrogen chloride (HCl), hydrogen bromide (HBr), hydrogen iodide (HI), and the like are mentioned. The above method has significant disadvantages in spite of its usability. The most important thing among those is additional considerable energy loss caused by pre-heating treatment at 300° C. or less for a long period, thereby extending entire processing time, and increasing energy consumption. In addition, the technical measures to apply gas-type halides for activation of process is not environmentally safe.

[26] includes pulverizing process of silicon, and interaction process of alcohol and ground silicon through a catalyst in a heated solvent environment with a reagent activated. Silicon is milled to fine particles to a size of 500 μm in the air using a ball mill. As an alcohol reagent, ethanol and methanol are used, and triethoxysilane and trimethoxysilane are obtained as a final product. As a catalyst, usually a copper-containing compound, mainly CuCl is used. As a solvent, polyaromatic oil is used, and the main technical process of an interaction between milled silicon and alcohol is performed under the environment where the solvent is heated to 200° C. The activation technique for an reagent is applied, and the reason for applying such technique is as follows: In the preparation of trialkoxysilane according to the illustrated schematic, impurities in raw materials are accumulated in reaction mass to make the consumption of reaction mass uneven, and solvent is partly consumed in a side reaction caused by impurities in raw materials, thereby generating unreacted silicon. Therefore, a technique to activate reagent is applied, which bleeds and participates a reaction mixture suspension containing unreacted silicon, and adds an adequate amount of solvent and catalyst, to return the concentrated suspension to the process. Such process is carried out several times during technical processing as unreacted silicon is accumulated in a reactor in the form of deposits. Like other similar methods, in spite of decrease in side reaction, increase in product yield, decrease in raw material loss, and increase in equipment productivity, the method has a technical disadvantage of having very complicated process, because the process is activated by applied technical measures, that is, separating unreacted silicon, and periodically repeated adding concentrated mixture of solvent and catalyst to reaction mass, in order to supplement the loss of solvent and catalyst. Moreover, since it is possible to rapidly reduce or slow down the reaction in the addition of an amount of new reagent instead of bled part, any measures followed by remove or shortening of reaction induction period are not considered.

RELATED ART DOCUMENT

Patent Document

[1] U.S. Pat. No. 5,260,471: Process for producing trialkoxysilane/Yashinori Yamada 1993.
[2] U.S. Pat. No. 3,072,700: Process for producing silanes/Nicolas P. V. de with 1963.
[3] Japanese Patent Laid-Open Publication No. 06-065258: Preparation of trialkoxysilanes/Harada, Masayoshi, Yamada, Yoshinori, 1994.
[4] U.K. Patent No. 2263113: Process for producing trialkoxysilanes/Yamada, Yoshinori, Harada, Katsuyoshi, 1993.
[5] Japanese Patent Laid-Open Publication No. 05-178864: Preparation of trialkoxysilanes/Yamada, Yoshinori, Harada, Masayoshi, 1993.
[6] U.S. Pat. No. 3,641,077: Method for preparing alkoxy derivatives of silicon germanium tin thallium and arsenic/Rochov E. G. 1972.
[7] U.S. Pat. No. 2,380,997: Contact masses/Patnode Winton. 1945.
[8] U.S. Pat. No. 2,473,260: Preparation of tetramethyl silicate/Rochov E. G. 1946.
[9] U.S. Pat. No. 4,314,908: Preparation of reaction mass for the production of methylchlorosilane/Downing James; Wells James, 1982.
[10] U.S. Pat. No. 4,727,173: Process for producing trialkoxysilanes/Mendicino F. D. 1988.
[11] U.S. Pat. No. 3,775,457: Method of manufacturing alkoxysilanes/Hisashi Muraoka, Yokohama, Kanagawa-ken. 27.11.73
[12] U.S. Pat. No. 4,762,939: Process for trialkoxysilane/tetraalkoxysilane mixtures from silicon metal and alcohol. 1988.
[13] U.S. Pat. No. 5,783,720: Surfase-active additives in the direct synthesis of trialkoxysilanes/Mendicino, Frank, Childress. 1998.
[14] U.S. Pat. No. 6,090,965: Removal of dissolvent silicates from alcohol-silicon direct synthesis solvents/K. M. Lewis, Hua Yu. 2000.
[15] U.S. Pat. No. 5,166,384 (US) Method for the removal of siloxane dissolved in the solvent employed in the preparation of trimethoxysilane via methanol-silicon metal reaction/Donald L. Bailey, Thomas E. Childress, Newport, both of Ohio. 1992.
[16] U.S. Pat. No. 5,362,897: Process for producing trialkoxysilane/Katsuyoshi Harada, Yashinori Yamada. 1994.
[17] U.S. Pat. No. 4,931,578: Process for the preparation of alkoxysilane/Yoshiro Ohta, Kamida-chou, Izumi-ku. 1990.
[18] Japanese Patent Laid-Open Publication No. 06-312994: Preparation of alkoxysilanes/Harada, Masayoshi, Yamada, Yoshinori. 1994.
[19] Japanese Patent Laid-Open Publication No. 06-312992: Preparation of alkoxysilanes/Harada, Masayoshi, Yamada Yoshinori. 1994.
[20] Japanese Patent No. (Sho)50-34540: Alkoxysilanes/Masafumi Asano, Kawasaki, Taizo Ohashi 1975.
[21] Japanese Patent No. (Sho)51-1692: Process for producing trialkoxysilanes/Hisashi Muraoka, Yokohama, Masafumi Asano, 1976.
[22] U.S. Pat. No. 5,177,234: Preparation of alkoxysilanes by contacting a solution of hydrogen fluoride in an alcohol with silicon/Binh T. Nguyen. 1993.
[23] U.S. Pat. No. 4,487,949: Process for preparation of alkyl silicates/Charles B. Mallon, Belle Mead, N.J., 1984.
[24] European Patent No. 517398: Preparation of alkoxysilanes using HF (salt) and silicon and alcohol/Bank, Speier, John Leopold, 1992.
[25] WO 2007/032865: PROCESS FOR THE DIRECT SYNTHESIS OF TRIALKOXYSILANE
[26] Russian Federation Patent No. 2235726 C1: Method for preparing alkoxysilanes/Gorshkov A. S., Markacheva A. A., Storozhenko P. A., 2003

DISCLOSURE

Technical Problem

In order to solve the above problems, an object of the present invention is to provide:

(i) removing or significant reducing induction period of synthesis reaction (ii) guaranteeing consistent removal of impurities contaminating solvent and acting as a catalyst of a side reaction, and products from a side reaction, from reaction environment; and (iii) ensuring synthesis reaction of trialkoxysilane in continuous mode.

Technical Solution

In one general aspect, a method for preparing trialkoxysilane includes:

(a) pulverizing silicon (Si) into fine particles having a size of 30-100 μm in a solvent environment, wherein the solvent is directly used in a later synthesis process of alkoxysilane;

(b) continuously synthesizing trialkoxysilane by continuously feeding a suspension of silicon and anhydrous alcohol in an amount consumed in a reaction in a synthesis process of trialkoxysilane to a reactor, wherein the amount of consumed suspension is calculated from an amount of synthesized trialkoxysilane using following Equation 1, so that an amount of silicon fed to a reactor as a suspension component, and an amount of silicon after a reaction is completed in a reaction process are maintained the same, thereby feeding a suspension so that a reaction proceeds consistently and stably, $$mSi = k1 \cdot mTES + k2 \cdot mTEOS \qquad \text{[Equation 1]}$$

wherein, mTES is mass of triethoxysilane, mTEOS is mass of tetraethoxysilane obtained per unit time as a result of direct reaction, and k1 and k2 are molar ratios of silicon consumed in synthesis processes of triethoxysilane and tetraethoxysilane, respectively; and (c) removing impurities accumulated in a reactor in a manner of continuously bleeding a solvent using a ceramic membrane filter from a reactor, wherein a solvent is supplemented by continuously feeding an amount of bled solvent as a suspension component to a reactor.

In addition, the object of the present invention is established by the following preferred embodiments:

The silicon may have a linear dimension of 20 mm to 20 cm prior to pulverizing.

A required amount of a catalyst may be directly put into a silicon mass in the pulverizing process in a solvent environment.

The catalyst may be used in an amount of 1.0-10.0 wt % relative to silicon.

A mass ratio of the solvent and the silicon may be 1:2 to 2:1.

The solvent may be heated to 160 to 300° C. in the synthesis process of trialkoxysilane.

The suspension may be continuously mixed before fed to a reactor, in order to maintain a stable ratio of the amounts of silicon, solvent and catalyst.

The amounts of the silicon, the solvent and the catalyst in a reaction environment may be constantly maintained throughout the entire synthesis processes of trialkoxysilane.

The solvent containing impurities formed therein as the reaction proceeds, may be bled through a ceramic membrane filter equipped in a reactor.

The ceramic membrane may have a pore size of 1 to 10 μm.

The solvent bled in a reaction environment may be used in the process through a purification operation.

Advantageous Effects

As described above, according to the present invention, in the raw material preparation, a silicon raw material is ground in a solvent environment without contact with air, so as to take an action for preventing the formation of oxide film on the surface of silicon; and in the technical process, by guaranteeing reaction activation, the initial induction period of the reaction of silicon and alcohol is dramatically shortened, unlike the prior arts, and thus, processing time is shortened, resulting in maximizing productivity, and making the method economical.

Moreover, since the pulverizing process of silicon which is a preparation operation of raw material is carried out in the environment using the same solvent as used in the later synthesis process, the technical process is not complicated but simplified, and since the consumed suspension is continuously fed, continuous process is possible.

Besides, wet process is used in pulverizing silicon, so that the generation of silicon fine dust having a risk of explosion during interaction with oxygen in the air is prevented, thereby securing stability, and the solvent is bled through a ceramic membrane filter to continuously remove impurities in reaction environment, thereby maintaining reaction conversion rate of silicon raw material consistently high without an additional process in continuous mode, and thus, making the method economical.

Therefore, since in the process for preparing trialkoxysilane, continuous synthesis process is possible through the reduction of induction period of direct synthesis reaction, and continuous removal of impurities, and thus, both dramatic shortening of entire processing time, and continuous production of trialkoxysilane are possible, the present invention may maximize productivity and economic efficiency.

DESCRIPTION OF DRAWINGS

FIG. 1 is a graph representing yields of reaction products (triethoxysilane; TES) over time in each Example according to the present invention and Comparative Example.

BEST MODE

The present invention provides a method for preparing trialkoxysilane including activation of reaction mass through interaction of anhydrous alcohol and silicon ground in the pulverizing process, in particular without contact with an atmosphere in a solvent environment, removal of impurities, and supplement of consumed amount of raw material, and trialkoxysilane may be synthesized through the following sequential steps:

(a) Silicon is ground into fine particles having a size of 30-100 μm in a liquid environment, preferably a solvent environment, wherein the liquid (or solvent) is directly fed and used as a solvent in a later synthesis process of trialkoxysilane. It is important that pulverizing is carried out in a liquid environment, more preferably, a solvent environment when considering reaction solvent to be used later.

(b) silicon is continuously fed to a reactor in a suspension state together with a solvent in an amount consumed in synthesis process of trialkoxysilane, wherein an amount of silicon fed to a reactor as a suspension component, and an amount of silicon after a reaction is completed in a reaction process are maintained the same, so that the progress of the reaction is maintained in consistent and stable state. In this case, the amount of consumed suspension and the amount fed as suspension are calculated from the amount of synthesized trialkoxysilane, by the above Equation 1.

(c) Impurities accumulated in the reactor is removed in a manner of continuously bleeding a solvent from the reactor using a ceramic membrane filter, wherein the solvent is continuously fed to the reactor as a suspension component in a bled amount, thereby guaranteeing supplement.

In the present invention, trialkoxysilane represented by the following Chemical Formula 1 may be preferably prepared.

SiH(OR)$_3$         [Chemical Formula 1]

wherein, R is methyl, ethyl, propyl or isopropyl group having 1 to 3 carbon atoms.

Physical basis of the technical measures suggested by the present invention in the first step of reagent activation is the condition where the silicon raw material is ground not in the air like the prior art method, but in a solvent environment, thereby preventing formation of natural oxide layer on the surface of silicon fine particles produced after pulverizing. The oxide layer is necessarily produced on the surface of all metal silicon when contacted with oxygen in the air. Such oxidation reaction is possible at all temperatures including room temperature, independently of chemical purity of silicon, that is, it may occur in any case where silicon is ground in the air as in prior art methods.

Meanwhile, natural oxides as mentioned above existing on the surface of ground silicon particles cause all the difficulties in the technical process for interaction of silicon and alcohol, which are generation of reaction 'induction period'; the requirement of heating a mixture of ground silicon in [1] and a catalyst; production of unreacted silicon from incomplete reaction; use of additional catalyst in the form of halides [1], or the requirement of recovering concentrated mixture into a reaction mass [26]; and consequently, very complicated technique and design of equipment.

In the case of the method suggested by the present invention, the main disadvantages of the prior art methods are excluded, since silicon is ground in a liquid environment, that is, solvent environment, so that there is no contact with atmosphere, and an oxide layer is not formed on the surface of silicon particles produced from pulverizing. That is, it has an active surface. There is no contact with an air, and at the same time, oxidation does not occur from the contact with a solvent. Later, the solvent is continuously used in the chemical reaction of the main technical process as its original use. In this way, the formation of oxide layer on the surface of the initial silicon particles is prevented by the technical measures according to the present invention, and thus, the activation of main technical process reagent, being prepared for immediate progress of synthesis reaction of trialkoxysilane, is guaranteed.

Besides, the ground fine particle size of the present method is 30-100 μm, which is up to 10 times smaller than [1] and [26], so that the contact area of main reagents is greatly increased, and consequently induction period is significantly shortened. In contrast, as suggested in practicing process of [26], similarly to [1], in case silicon is ground to such a small size in the air, since natural oxide film is formed on the surface of silicon, in the state of having significantly increased total surface area as compared to unground silicon, which is caused by making the size of fine particles small, induction period is increased, and other disadvantageous characteristics are strengthened.

Another main disadvantage of [26] is that reaction mixture is concentrated over many times by newly adding reagents to unreacted silicon, and for this, deposits in the suspension should be periodically bled, and long term precipitation is required. The present invention solves this problem by carrying out such operation in continuous manner. Herein, the present invention uses bleeding process of a suspension through a ceramic membrane filter in order to prevent coarse fine particles of silicon having reactivity from being removed from the reactor. The amount of silicon fed to the reactor as a suspension component is maintained the same as the amount of reacted silicon, and the amount of reacted silicon is determined by the amount(s) of synthesized trialkoxysilane and/or hydrogen formed as a result of the reaction. Solvent is continuously bled in the outlet of the reactor, and the solvent is fed to the reactor in the bled amount as a suspension component, to supplement bled amount, thereby removing impurities in the reactor.

By selecting 20 mm or more, preferably 20 mm to 20 cm as a linear dimension prior to pulverizing, the possibility that significant amount of silicon fine particles, on the surface of which oxides exist, are put into the reaction mixture, may be certainly prevented.

The characteristics represented by adding a catalyst to silicon mass prior to pulverizing of silicon are as follows: First, two materials are ground into the same size. Second, the above materials are homogeneously mixed within the suspension in the solvent environment in which silicon was ground as characterized by the present invention. The pore size in a ceramic membrane filter is 1 to 10 μm. If the pore size is smaller than 1 μm, filtering is difficult, and if larger than 10 μm, silicon fine particles having reactivity is removed through a filter, and loss of silicon increases. If the initial size of silicon fine particles is 30 to 100 μm, adequate pore size in ceramic membrane filter is 5 μm, wherein total loss of silicon is less than 0.5%.

The method of the present invention may be realized as follows: For example, initial silicon which is metal silicon having a purity of 98-99% is ground into a desired size using a hammer mill (particle size ~1 mm) and a general planetary ball mill, and working capacity is previously filled with a solvent. The solvent functions as thermal oil, and as such solvent, for example, alkylated benzene, alkylated naphthalene, polyaromatic oil, and the like may be used, preferably, as in [26] and other similar methods, THERMINOL® 66 or other polyaromatic oil may be used. According to the present invention, in the solvent environment, silicon pulverizing process is carried out until the fine particle size is reached to 30-100 μm, and obtained suspension is continuously fed to the reactor using dosing pump, so that the interaction of silicon and alcohol continuously occurs, but silicon powders are not separated from the solvent. In the reactor, planned capacity and contact mass of the components are formed.

The suspension component added for consistently maintaining the reaction in an amount consumed in the synthesis process includes silicon, corresponding solvent and catalyst, and the amount of silicon is calculated from the amount of synthesized trialkoxysilane using Equation 1. The suspension is consistently and stably fed into the reaction.

As anhydrous alcohol, anhydrous ethanol or anhydrous methanol which are well known in the art, may be used. In addition, as a catalyst, copper-containing catalyst such as CuCl may be used.

The main process is carried out at temperature ranging 180-260° C. as in [26], under a environment of a solvent having high boiling point such as THERMINOL® 59, THERMINOL® 60, THERMINOL® 66, DOWTHERM® HT, MARLOTHERM® S, MARLOTHERM® or other polyaromatic oil, as mentioned above. That is, the core of the main technical process is to fill reaction capacity in any well-known form with a suspension (catalyst-added silicon, for example, including ground silicon and CuCl powders in an environment of a solvent such as THERMINOL® 66), then strongly mix the mixture with heating to 180-260° C., and adding alcohol such as ethanol or methanol. Generated vapor-gas mixture and liquid are continuously removed from reaction capacity, and separated by any well-known technical method including those used in [1], [26], or other similar methods. Triethoxysilane to be desired or trimethoxysilane is also separated by such general methods.

The present invention may continuously bleed a solvent using a ceramic membrane filter, differently from the prior arts, and in particular, induction time may be dramatically shortened through the difference of pulverizing process of silicon raw material.

As mentioned above, in the prior arts, since silicon raw material are ground in the air, and the oxide film is inevitably formed on the surface of silicon, the existence of induction period which is the most important factor in the synthesis of trialkoxysilane is inevitable. Induction period is also necessarily undergone when in later continuous process, suspension is bled to additionally feed raw material. However, in the present invention, initial synthesis induction period which is inevitable in the synthesis of trialkoxysilane, may be removed or dramatically shortened, and using a ceramic membrane, impurities may be continuously removed in continuous process.

Meanwhile, according to the present invention, in case of carrying out only process (a), and using conventional method as the rest of synthesis processes, significant improvement is confirmed, and in case of carrying out only processes (a) and (b), and not process (c), also excellent effect is confirmed. Therefore, the cases where process (b) or processes (b) and (c) are omitted are also understood as improved inventions, respectively.

Hereinafter, the present invention will be described in detail by the following Examples, but is not limited thereto.

The Examples of the present invention are based on the experimental results in a specially designed equipment for synthesis of trialkoxysilane.

Example 1

The preparation of triethoxysilane was carried out in a reactor having working capacity of 9 L, which was equipped with an electric heating control device of reaction capacity, and an impeller stirrer having 4 wings to control rotational speed to 300-1500 rpm. 3.3 kg of metal silicon was ground in a solvent environment of 6.6 kg of THERMINOL® 66 using Planetary Mill until the particle size is 30-100 μm. In the pulverizing process, 0.2 kg of CuCl catalyst was put into the suspension. In the state of continuous operation of the stirrer at 850 rpm, contact mass was heated to temperature of 242+2° C., the feed of ethanol as anhydrous alcohol to the reactor was started at 600 ml/hr using dosing pump (Digital dosing pump), GRUNDFOS® DME 60-10 AR. Samples were taken when liquid product was generated in the reactor, then every 30 minutes. As a result of analysis of the samples in Gas chromathograph, Agilent® GC7890A, synthesis reaction was started 10 minutes after alcohol was poured, and reaction rate increased for initial 60 minutes. The synthesis reaction rate of triethoxysilane decreased after 180 minutes, and completely slowed down 260 minutes after alcohol was fed. Herein, 1635 g of triethoxysilane and 105 g of tetraethoxysilane were obtained. The selectivity of triethoxysilane was 94%.

Comparative Example

This experiment is carried out in the same condition as Example 1, except for the preparation process of reaction reagent. Metal silicon was ground in the air using Planetary Mill until the particle size is 30-100 μm. 3.3 kg of ground silicon, 6.6 kg of THERMINOL® 66 as a solvent, and 0.2 kg of CuCl catalyst were put into the reactor, and the reaction was started. As a result of analysis of the samples, the reaction of metal silicon and ethyl alcohol was started 150 minutes after alcohol was fed, then reaction rate gradually increased. The synthesis reaction of triethoxysilane was slowed down 500 minutes after alcohol was fed. For 500 minutes, 1435 g of triethoxysilane, and 614 g of tetraethoxysiane were obtained. The selectivity of triethoxysilane was 70%.

Example 2

This experiment was carried out in the same condition as Example 1, except that in the reaction with anhydrous ethanol, silicon was continuously fed to the reactor, depending on the amount of consumed solvent, in the state of mass ratio of solvent and silicon in suspension components of 2:1. In the synthesis process of trialkoxysilane, silicon of suspension component was fed to the reactor, and as a result of reaction, it was fed in the same rate as the consumption rate of silicon. The amount of consumed silicon per time unit was calculated from reaction mass-balance according to a formula such as above Equation 1.

$$mSi = k1 \cdot mTES + k2 \cdot mTEOS$$

wherein, mTES is mass of triethoxysilane, mTEOS is mass of tetraethoxysilane obtained per unit time as a result of a direct reaction, and k1 and k2 are coefficients related to molar ratios of silicon consumed in synthesis processes of triethoxysilane and tetraethoxysilane, respectively. In the present Example, it was confirmed that k1=0.171, and k2=0.135. As described above, silicon as a suspension component was continuously put into the reactor in the amount calculated from above Equation 1. At the same time, solvent was continuously bled through a ceramic membrane filter equipped in the reactor body. The solvent in which impurities dissolved was collected in a collection container for recycling. After filtering unreacted silicon and catalyst by forming vacuum to 10 mbar from the back of the ceramic membrane filter, the solvent was discharged. Herein, the solvent was continuously discharged through a ceramic membrane from the reactor, and its output was double of mSi specified according to above Equation 1, which is equal to the amount of solvent fed in the reactor as a suspension component. With this, contact mass components, and the levels of the above components in the reactor are maintained constant. The sample in the reactor was bled every 3 hours, and contact mass components were controlled. The level of contact mass in the reactor was visually confirmed through a window of the reactor. Synthesis reaction was started 10 minutes after alcohol was fed to the reactor, and the reaction rate sharply increased for initial 60 minutes, then slowly increased for 120 minutes, and was stabilized at triethoxysilane synthesis level of 420-450 g/h. For 500 minutes, 600 g of silicon and 1200 g of THERMINOL® 66 solvent were continuously fed as suspension components. During this period, 3380 g of triethoxysilane and 141 g of tetraethoxysilane were obtained. The selectivity of triethoxysilane was 96%.

Example 3

In this experiment, under the same condition as Example 2, the amount of silicon consumed in the reaction of silicon and anhydrous ethanol was calculated through Equation 1, and silicon was continuously fed to the reactor in the state of mass ratio of solvent and silicon in suspension components of 2:1. Difference was that a ceramic membrane filter was not equipped, and the solvent was not bled. Synthesis reaction was started 9 minutes after alcohol was fed to the reactor, and the reaction rate increased for first 90 minutes, then was stabilized at the level of trietoxysilane of 400 g/h. Reaction was stopped 250 minutes after feed of alcohol was started, by generation of large amount of foam in the reaction product. During this period, 290 g of silicon and 580 g of THERMINOL® 66 catalyst were continuously fed to the reactor as suspension components. Additional input of the solvent caused the increase in the amount of contact mass in the reactor, and generated foam in the reactor. For 250 minutes of reaction, 1600 g of triethoxysilane and 120 g of tetraethoxysilane were obtained. The selectivity of triethoxysilane was 93%.

Following Table 1 shows the results of comparison of Examples and Comparative Example.

TABLE 1

| Example | Pulverizing method of silicon powder | Time taken to start Reaction after feeding ethanol (induction period, minute) | Fed amount | | | Results | | |
|---|---|---|---|---|---|---|---|---|
| | | | MG Si (g) | Solvent (g) | Bled amount Solvent (g) | TES productivity (g) | TEOS productivity (g) | TES selectivity |
| Example 1 | Solvent environment | 10 | — | — | — | 1635 | 105 | 93 |
| Comparative Example | In the air | 150 | — | — | — | 1435 | 614 | 70 |
| Example 2 | Solvent environment | 10 | 600 | 1200 | 1200 | 3380 | 141 | 96 |

TABLE 1-continued

| Example | Pulverizing method of silicon powder | Time taken to start Reaction after feeding ethanol (induction period, minute) | Fed amount | | Bled amount Solvent (g) | Results | | |
|---|---|---|---|---|---|---|---|---|
| | | | MG Si (g) | Solvent (g) | | TES productivity (g) | TEOS productivity (g) | TES selectivity |
| Example 3 | Solvent environment | 9 | 290 | 580 | — | 1600 | 120 | 94 |

As described above, the biggest difference of the technical measures suggested by the present invention from the prior art methods is, that in the raw material preparation, a silicon raw material is ground in a liquid environment, so as to take an action for preventing the formation of oxide film on the surface of silicon; and in the technical process, by guaranteeing reaction activation (Examples 1, 2 and 3), the initial induction period of the reaction of silicon and alcohol is dramatically shortened, unlike the prior arts, and thus, processing time is shortened, resulting in maximization of productivity, and making the present invention economical.

In addition, in case of feeding suspension (Examples 2 and 3), good effects as compared to Comparative Example, such as TES productivity, TES selectivity, dramatic shortening of initial induction period, and the like were confirmed. In case of also bleeding solvent (Example 2), very good effect of at least double the TES productivity of Comparative Example for the same reaction time was shown.

The technical solution suggested by the present invention is simply realized using prior art equipments, and since above mentioned preparation of raw material (pulverizing silicon) is carried out in a solvent environment, that is, in an environment using a material which is used as a solvent in a later technical process, the technical process is not complicated, but simplified.

In addition, since the pulverizing process of silicon which is a preparation operation of raw material is carried out in the environment using the same solvent as used in the later synthesis process, the technical process is not complicated and simplified, and since the consumed suspension is continuously fed, and continuous synthesis process through consistent removal of impurities using a ceramic membrane filter, is possible, entire processing time is dramatically shortened, and at the same time, trialkoxysilane is continuously prepared, thereby maximizing productivity and economic efficiency.

Summarizing the above description, the technical measures of the present invention have the following effects:
  Reduction of induction period of direct synthesis reaction;
  Continuation of synthesis reaction of trialkoxysilane; and
  Continuous removal of impurities in reaction environment by bleeding solvent through a ceramic membrane filter.
Therefore, all technical problems are solved by realizing the method of the present invention.

The invention claimed is:

1. A method for preparing trialkoxysilane comprising:
  (a) pulverizing silicon (Si) into fine particles having a size of 30-100 μm in a solvent environment, wherein the solvent is directly used in a later synthesis of alkoxysilane;
  (b) continuously synthesizing trialkoxysilane by continuously feeding a suspension of silicon and anhydrous alcohol in an amount consumed in a reaction in a synthesis process of trialkoxysilane to a reactor, wherein the amount of consumed suspension is calculated from an amount of synthesized trialkoxysilane using following Equation 1, so that an amount of silicon fed to a reactor as a suspension component, and an amount of silicon after a reaction is completed in a reaction process are maintained the same, thereby feeding a suspension so that a reaction proceeds consistently and stably, $$mSi = k1 \cdot mTES + k2 \cdot mTEOS \qquad \text{[Equation 1]}$$

wherein, mSi is mass of silicon to feed to a reactor as a suspension component
    mTES is mass of triethoxysilane obtained per unit time,
    mTEOS is mass of tetraethoxysilane obtained per unit time,
    k1 is atomic weight of Si/molar mass of TES obtained per unit time, and
    k2 is atomic weight of Si/molar mass of TEOS obtained per unit time; and
  (c) removing impurities accumulated by continuously bleeding a solvent using a ceramic membrane filter.

2. The method of claim 1, wherein the silicon has a linear dimension of 20 mm to 20 cm prior to pulverizing.

3. The method of claim 1, wherein a mass ratio of the solvent and the silicon is 1:2 to 2:1.

4. The method of claim 1, wherein the catalyst is directly put into a silicon mass in an amount of 1.0 to 10.0 wt % in the pulverizing process in a solvent environment.

5. The method of claim 4, wherein the catalyst is a copper-containing catalyst.

6. The method of claim 1, wherein the solvent is heated to 160 to 300° C. in the synthesis process of trialkoxysilane.

7. The method of claim 1, wherein
  in the pulverizing of silicon, a copper-containing catalyst is used,
  anhydrous methanol or anhydrous ethanol is used as the anhydrous alcohol, and
  in the synthesis of trialkoxysilane, the solvent is heated to 160 to 300° C., while steps (a), (b) and (c) subsequently proceed.

8. The method of claim 1, wherein the suspension is continuously mixed before fed to a reactor, in order to maintain a stable ratio of silicon, solvent, and catalyst.

9. The method of claim 1, wherein the solvent is bled through a ceramic membrane filter equipped in a reactor body in a reaction process with impurities dissolved in the solvent.

10. The method of claim 1, wherein the ceramic membrane has a pore size of 1 to 10 μm.

11. The method of claim 1, wherein the amounts of the silicon, the solvent, and the catalyst in a reaction environment are constantly maintained throughout the entire synthesis processes of trialkoxysilane.

12. The method of claim 1, wherein the trialkoxysilane is represented by following Chemical Formula 1:

$$SiH(OR)_3 \qquad \text{[Chemical Formula 1]}$$

wherein, R is methyl, ethyl, propyl or isopropyl group having 1 to 3 carbon atoms.

* * * * *